US011661407B2

(12) United States Patent
Somappa et al.

(10) Patent No.: US 11,661,407 B2
(45) Date of Patent: May 30, 2023

(54) PROCESS FOR THE PREPARATION OF PYRYLIUM SALTS

(71) Applicant: COUNCIL OF SCIENTIFIC AND INDUSTRIAL RESEARCH, New Delhi (IN)

(72) Inventors: Sasidhar Balappa Somappa, Thiruvananthapuram (IN); Chettiyan Thodi Fathimath Salfeena, Thiruvananthapuram (IN); Ayyappanpillai Ajayaghosh, Thiruvananthapuram (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/967,613

(22) PCT Filed: Dec. 31, 2018

(86) PCT No.: PCT/IN2018/050898
§ 371 (c)(1),
(2) Date: Aug. 5, 2020

(87) PCT Pub. No.: WO2019/155485
PCT Pub. Date: Aug. 15, 2019

(65) Prior Publication Data
US 2021/0087158 A1 Mar. 25, 2021

(30) Foreign Application Priority Data
Feb. 6, 2018 (IN) .............................. 201811004385

(51) Int. Cl.
C07D 309/34 (2006.01)
B01D 5/00 (2006.01)

(52) U.S. Cl.
CPC ........... C07D 309/34 (2013.01); B01D 5/006 (2013.01)

(58) Field of Classification Search
None
See application file for complete search history.

(56) References Cited

U.S. PATENT DOCUMENTS

| | | | |
|---|---|---|---|
| 3,250,615 | A | 5/1966 | Allan et al. |
| 3,417,083 | A | 12/1968 | Reynolds et al. |
| 3,462,706 | A | 8/1969 | Ammons et al. |
| 3,615,396 | A | 10/1971 | Gramza et al. |
| 3,938,994 | A | 2/1976 | Reynolds et al. |
| 4,451,659 | A | 5/1984 | Potts |
| 2002/0065192 | A1* | 5/2002 | Mackenzie ............. C08F 10/00 502/167 |

OTHER PUBLICATIONS

Grant & Hackh's Chemical Dictionary (5th Ed. 1987).*
International Searching Authority, International Search Report and Written Opinion for International Application No. PCT/IN2018/050898, dated Mar. 19, 2019, (10 pages), Indian Patent Office, New Delhi, India.
International Preliminary Examining Authority, International Preliminary Report on Patentability for International Application No. PCT/IN2018/050898, dated Mar. 3, 2020, (50 pages), New Delhi, India.
Bos, H.J.T. et al. *Addition of Carbonyl Compounds to Alkynes Under the Influence of Boron Trifluoride*, Recueil des Travaux Chimiques des Pays-Bas, Feb. 28, 1963, vol. 82, Issue 9, pp. 845-858. DOI: 10.1002/recl.19630820903.
Kadayat, Tara Man et al. *Synthesis, Topoisomerase I and II Inhibitory Activity, Cytotoxicity, and Structure-Activity Relationship Study of 2-Phenyl-or Hydroxylated 2-Phenyl-4-Aryl-5H-Indeno[1, 2-b] Pyridines*, Bioorganic & Medicinal Chemistry, Jul. 1, 2015, vol. 23, Issue 13, pp. 3499-3512. DOI: 10.1016/j.bmc.2015.04.031.
A. Dinculescu et al., "Synthesis of Pyrylium Salts with Various Anions," Bulletin des Sociétés Chimiques Belges, 100(9):665-672, (1991).
A. M. Bonch-Bruevich et al., "Absorption and Fluorescent Properties of Pyrylium Compounds: I. The Nature of Electronic Transitions and Structural Rearrangement in the Excited State," Optics and Spectroscopy, 89(2):216-224, (2000).
Edwin Alfonzo et al., "Redesign of a Pyrylium Photoredox Catalyst and Its Application to the Generation of Carbonyl Ylides," Organic Letters, 19:2989-2992, (2017).
F. P. Schäfer et al., "New Dye Lasers Covering the Visible Spectrum," Physics Letters, 24A(5):280-281, (Feb. 1967).
Gui Ling Ning et al., "Conversion of Phenyl-Substituted Cyclopentadienes to Pyrylium Cations," Journal of Organic Chemistry, 69(4):1432-1434, (2004).
J. A. Vanallan et al., "The Preparation of Certain Pyrylium Salts by Using Chalcone and Boron Trifluoride Etherate," The Journal of Organic Chemistry, 33(3):1102-1105, (Mar. 1968).

(Continued)

*Primary Examiner* — Po-Chih Chen
(74) *Attorney, Agent, or Firm* — Alston & Bird LLP

(57) ABSTRACT

The present invention relates to the process for the preparation of Pyrilium salts having the formula represented below. Present invention provide a simplified method of producing symmetrical and unsymmetrical pyrylium salts. The invention explores readily available starting materials with reaction conditions which are suitable for industrial scale applications. All the synthesized compounds were confirmed by various spectroscopic techniques such as Fourier transform infrared spectroscopy, 1H NMR, 13C NMR, 19F NMR spectroscopy, and single-crystal X-ray analysis. Mass of the compounds confirmed by HRMS analysis.

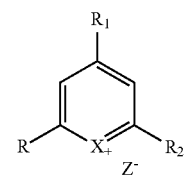

6 Claims, 3 Drawing Sheets

(56) References Cited

OTHER PUBLICATIONS

Jinlong Zhang et al., "Synthesis of Some New Thiapyrylium and Pyrylium Laser Dyes," Dyes and Pigments, 27(4):263-269, (1995).

Lijian Yang et al., "Highly efficient one-pot synthesis of α-free pyrylium salts with tunable fluorescence emission via ring-expanding reaction of triarylcyclopentadienes," Tetrahedron Letters, 54:2967-2971, (2013).

Miguel A. Miranda et al., "2,4,6,-Triphenylpyrylium Tetrafluoroborate as an Electron-Transfer Photosensitizer," Chemical Reviews, 94(4):1063-1089, (1994).

Peter Nikolov et al., "Peculiarities in the photophysical properties of some 6-styryl-2,4-disubstituted pyrylium salts," Journal of Photochemistry and Photobiology A: Chemistry, 135: 13-25, (2000).

Tomasz Kotowski et al., "Pyrylium and thiopyrylium high efficiency laser dyes," Journal of Luminescence, 50:39-45, (1991).

W. C. Dovey et al., "Triarylpyrylium Borofluorides," 1389-1390, (1935).

W. Dilthey, "On pyrylium compounds. III," Journal of Practical Chemistry, 1008-1010, (1917). (Eng. translation only).

Zofia Dega-Szafran et al., "Kinetics and Mechanisms of Nucleophilic Displacements with Heterocycles as Leaving Groups. Part 20.[1] Aggregation of Some Quaternary Pyridinium Salts in Chlorobenzene," Journal of the Chemical Society, Perkin Transactions II, 1895-1897, (1985).

* cited by examiner

PROCESS FOR THE PREPARATION OF PYRYLIUM SALTS

CROSS REFERENCE TO RELATED APPLICATIONS

This application is a National Stage Application, filed under 35 U.S.C. § 371, of International Application No. PCT/IN2018/050898, filed Dec. 31, 2018, which claims priority to Indian Application No. 201811004385, filed Feb. 6, 2018; the contents of both of which are hereby incorporated by reference in their entirety.

BACKGROUND

Related Field

The present invention relates to the process for the preparation of Pyrylium salts. Present invention provide a simplified method of producing symmetrical and unsymmetrical pyrylium salts. The invention explores readily available starting materials with reaction conditions which are suitable for industrial scale application's. All the synthesized compounds were confirmed by various spectroscopic techniques such as Fourier transform infrared spectroscopy, 1H NMR, 13C NMR, 19F NMR spectroscopy, and single-crystal X-ray analysis. Mass of the compounds confirmed by HRMS analysis.

Description of Related Art

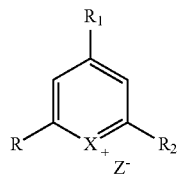

FIG 1

Pyrylium salts demonstrate wide spread applications in many fields, such as, photosensitizers [see Miranda et al, Chem. Rev., 1994, 94, 1063; Alfonzo et al, Org. Lett., 2017, 19, 2989], Qswitchers [see U.S. Pat. No. 3,417,083 by Reynolds et al; U.S. Pat. No. 3,462,706 by Ammons et al.], laser dyes [see Schafer et al, Phys. Lett., 1967, 24A, 280; Kotowski et al, J. Lumin., 1991, 50, 39; Zhang et al, Dyes Pigm., 1995, 27, 263], and organic luminophores [see Bonch-Bruevich et al, Opt Spectrosc., 2000, 89, 216; Nikolov et al, J. Photochem. Photobiol. A, 2000, 135, 13]. It is also mentioned that such salts enhance the efficiency and effectiveness of photoconductive compositions [see U.S. Pat. No. 3,938,994 by Reynolds et al; U.S. Pat. No. 3,615,396 by Gramza et al; and U.S. Pat. No. 3,250,615 by Van Allan et al].

Various methods are known for the preparation of pyrylium and related salts. Such processes are related to methods of preparing a larger class of substituted pyridines which contains the class of pyrylium salts. Among the numerous ways to prepare substituted pyrylium salts discussed in the literature [see Vanallan et al, J. Org. Chem., 1968, 33, 1102; Dilthey et al, J. Pr. Chem., 1916, 94, 53; Dinculescu et al, Bull. Soc. Chim. Belg., 1991, 100, 665; Dovey, et al, J. Chem. Soc., 1935, 1389; Katritzki et al, J. Chem. Soc., Perkin Trans., 1980, 1895; Bos et al, RECUEIL, 1963, 82, 845; Ning et al, J. Org. Chem., 2004, 69, 1432; Yang et al, Tetrahedron Lett., 2013, 54, 2967; Potts et al, U.S. Pat. No. 4,451,659, Issued on 29 May 1984].

In general, the existing prior arts lead to the synthesis of either symmetrical or unsymmetrical pyrylium salts. And multiple steps are involved in the preparation of unsymmetrical pyrylium salts. Whereas, the disclosed invention is a simplified, a versatile direct synthesis of producing symmetrical and unsymmetrical pyrylium salts. The method produces those types of salts which have a displaceable substituent in the fourth position which allows the attachment of such salts, by displacement of this group to a variety of organic substituent or supports. The invention explores readily available starting materials with reaction conditions which are suitable for industrial scale applications. A notable features of the invention are, R, $R_1$, $R_2$, can be of same substitution or of different substitutions, column chromatography free separations and Z− can be displaceable by $BF_{4-}$, $oTf^-$, $ClO_{4-}$.

In comparison with prior arts, the present invention discloses hitherto unknown and known pyrylium salts and a simplified method of preparation.

BRIEF SUMMARY

Main objective of the present invention is to provide an efficient catalytic two step process for the synthesis of variety of symmetrical and unsymmetrical pyrylium salts.

Another objective of the present invention is to provide a industrially viable and cost effective process for the preparation of symmetrical and unsymmetrical pyrylium salts.

Yet another objective is to provide a notable versatility in the substituents incorporated into these pyrylium salts and at the same time provide a direct and efficient synthesis of these salts.

Still another objective is to provide a novel photosensitive system and which produce a marked increase in sensitivity at longer wave length of the visible light spectrum.

Yet another objective is to prepare those types of salts which have a displaceable substituent ($X^+$ and $Z^−$), which allows the attachment of such salts, by displacement of this group to a variety of organic substituent or supports.

DETAILS OF ABBREVIATIONS

NMR—Nuclear Magnetic Resonance
HRMS—High resolution mass spectrometry
KOtBu—Potassium tert-butoxide
KOH—Potassium hydroxide
DCM—Dichloromethane
$BF_3.OEt_2$—Boron trifluoride diethyl etherate

SUMMARY OF THE PRESENT INVENTION

This invention relates to a convenient and practical synthesis of a variety of pyrylium salts of general formula I.

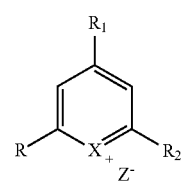

FIG 1

Where X is oxygen; R, $R_1$, $R_2$, represents phenyl radicals with various substitution, such as, $CH_3$, $OCH_3$, OH, Br, Cl, F, $CF_3$; R, $R_1$, $R_2$, represents heteroaryl radicals such as thiophene, furan, containing a variety of substitutions. R also represents bulky groups such as naphthylradicals, R also contains fused substitutions like, fused cyclohexyl and octahydronaphthalenyl radicals. $R_2$ also represents phenyl radicals substituted with alkyl chain of three carbon atoms and $Z^-$ is an anionic function such as $BF_{4-}$, $ClO_{4-}$.

In an aspect of the present invention, where in the halide substituted α,β-unsaturated ketones comprises Cl, Br, F.

In another aspect of the present invention, where in the other than halide substitutions of α,β-unsaturated ketones comprises $CH_3$, $OCH_3$, OH, $CF_3$.

In yet another aspect of the present invention, where in α,β-unsaturated ketones comprises naphthyl substitutions.

In still another aspect of the present invention, where in α,β-unsaturated ketones comprises of heterocycles such as furans and thiophenes.

In another aspect of the present invention, where in the arylidene ketones comprising the cyclohexyl and octahydro naphthalenyl substitution.

In yet another aspect of the present invention, where in halide substituted phenyl acetylene comprises of Cl, Br, F.

In still another aspect of the present invention, where in the phenyl acetylenes comprises of alky chain of three carbon atoms.

In another aspect of the present invention, where in the acetylenes are substituted with heterocyclic thiophene.

In yet another aspect of the present invention, where in 3 equivalents of lewis acid comprises 3 equivalents of $BF_3.OEt_2$.

In still another aspect of the present invention, where in Z- is one of, $BF_{4-}$, $OTf^-$, $ClO_{4-}$.

In another aspect of the present invention, wherein present invention provide a novel photosensitive system which produce a marked increase in sensitivity at longer wave length of the visible light spectrum.

In yet another aspect of the present invention, all the products are subjected to purification by filtration, crystallization, distillation or extraction.

The various features of novelty which characterise the invention are pointed out with particularity in the claims annexed to and forming a part of this disclosure. For better understanding of the present invention, its operational advantages and specific objectives attained by its uses, reference is made to the accompanying descriptive material in which preferred embodiments of the invention are illustrated.

Technical problem to be solved by this invention is improved process through the four component, two-step process involving the synthesis of α-,β-unsaturated ketones followed by the cyclisation of these α,β-unsaturated ketones with various substituted alkynes in the presence of $BF_3.OEt_2$ will provide a pyrylium salts.

DETAILED DESCRIPTION OF THE INVENTION

Figure 1:
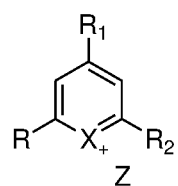
FIG. 1 represents the general structure of the pyrylium ion

The present invention relates to the process for the preparation of Pyrylium salts. Present invention provide a simplified method of producing symmetrical and unsymmetrical pyrylium salts. The present process provide a notable versatility in the substituents incorporated into these pyrylium salts and at the same time provide a direct and efficient synthesis of these salts. Present invention provide a novel process of pyrylium salts preparation by condensing an acetophenone with aldehyde in the presence of NaOH, treating the resultant product with phenyl acetylenes or heterocyclic appended acetylenes in the presence of $BF_3.OEt_2$ to form the cyclised product of pyrylium salts. Other strong bases like KOtBu, KOH may be used to generate the enolate of the methyl ketone for the reaction with aldehyde to form α,β-unsaturated ketones in a variety of solvents such as Ethanol, Methanol, DCM. In one of the embodiment of the invention, the process used is a four component, two-step involving the synthesis of α,β-unsaturated ketones (Examples shown in the examples section) followed by the cyclisation of these α,β-unsaturated ketones with various substituted alkynes in the presence of $BF_3.OEt_2$ will provide a pyrylium salts of the formula (FIG. 1).

Figure 2:
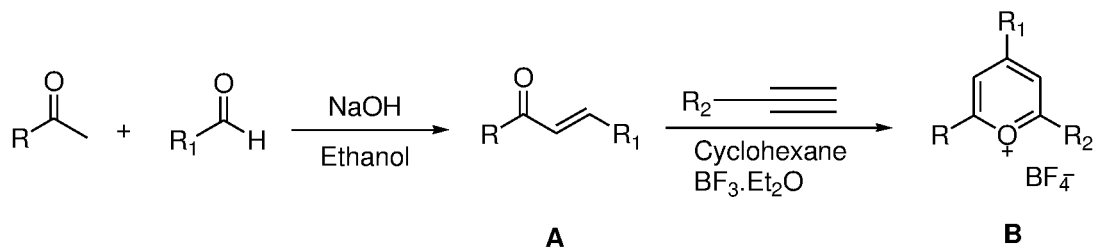
FIG. 2 represents the schematic diagram depicting the process protocol to prepare pyrylium ions

In another embodiment of the invention, alternatively, after the preparation of α,β-unsaturated ketones, to the same reaction vessel $BF_3.OEt_2$ and various substituted alkynes will be added to facilitate the cyclisation in one pot three component fashion. As generally shown in reaction (FIG. 2).

In still another embodiment of the invention, acetophenones on condensation with aldehydes in presence of NaOH in ethanol will yield the α,β-unsaturated ketones (A). The intermediate product A was added to an aryl or heteroaryl acetylenes and $BF_3.OEt_2$ in dry cyclohexane at 60-70° C., and stirred for 3-6 hrs under the oxygen atmosphere. After the completion of reaction, the reaction mixture was poured in to diethyl ether to precipitate the product. The product is filtered off, washed with diethyl ether, dried in air and crystallised from ethanol to get the crystalline pyrylium salts (B).

Figure 3:
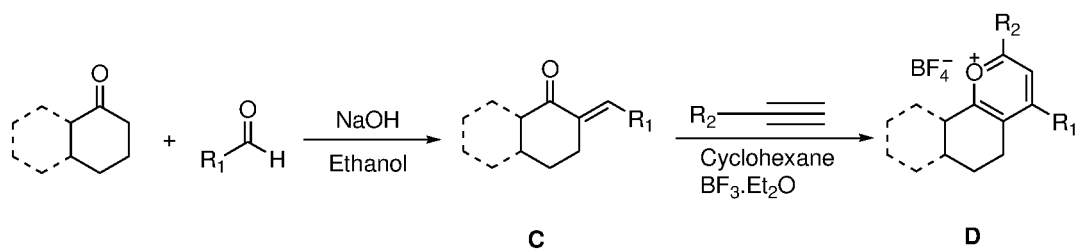
FIG. 3 represents the schematic diagram depicting the process protocol to prepare fused-pyrylium ions
Figure 4:
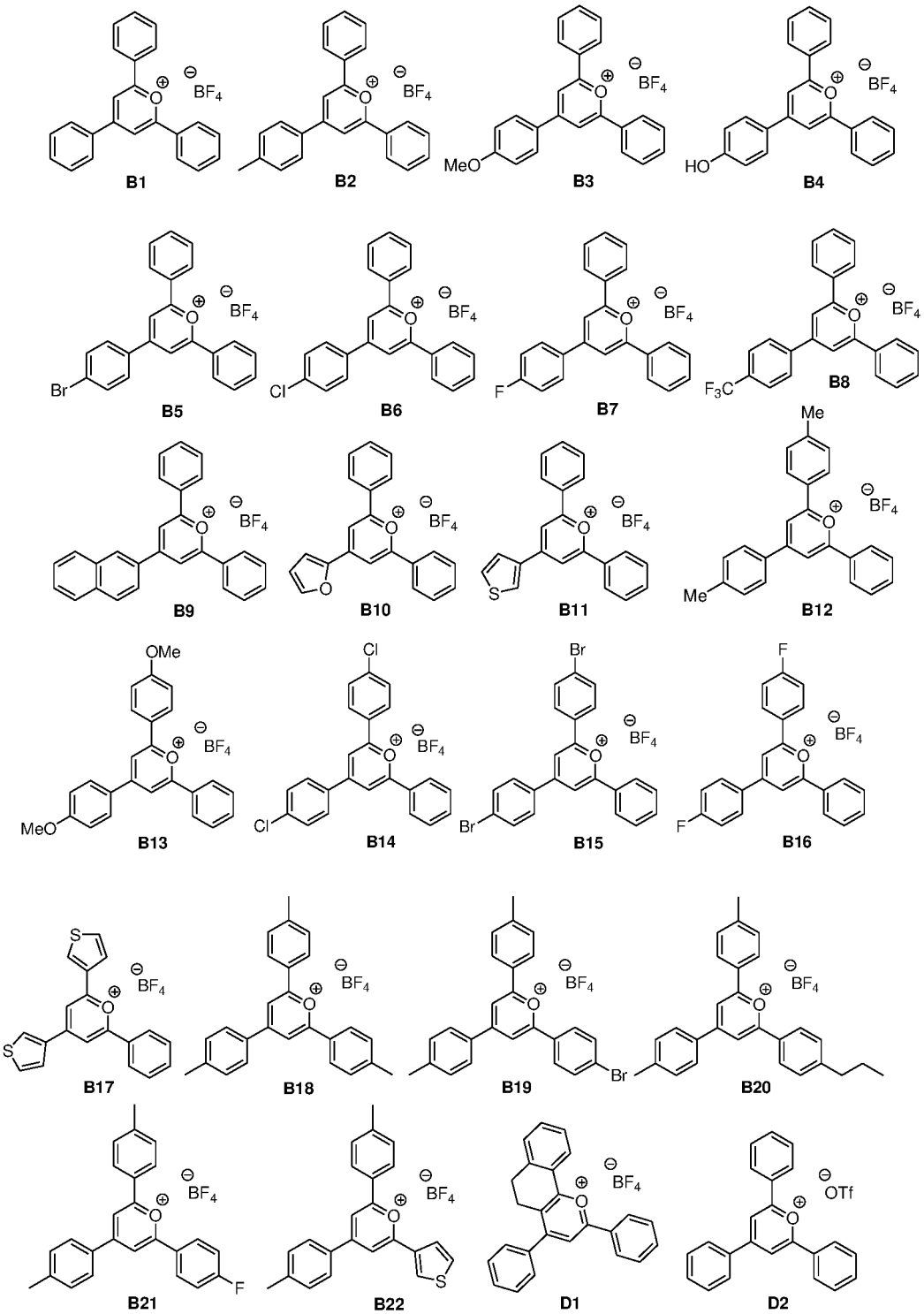
FIG. 4 represents the library of compounds synthesized through the invented protocol.
Figure 5:
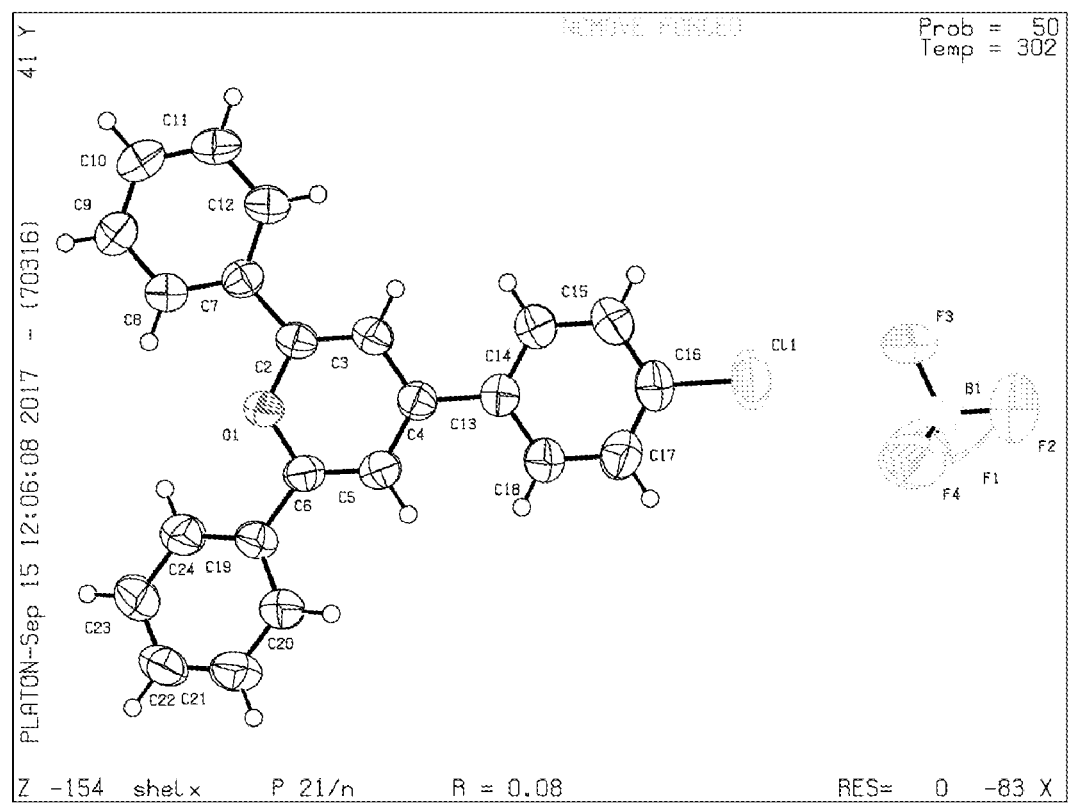
FIG. 5 represents Single-Crystal X-Ray structure for compound B6 (CCDC 1574744)

In yet Another embodiment of the invention, novel process also illustrated for the preparation of fused pyrylium salts. Arylidene ketones (C) was added to an aryl or heteroaryl acetylenes and $BF_3.OEt_2$ in dry cylcohexane at 60° C., and stirred for 3-6 hrs under the oxygen atmosphere. After the completion of reaction, the reaction mixture was poured in to diethyl ether to precipitate the product (D) and crystallised from ethanol to get the crystalline compounds (FIG. 3).

In another embodiment of the invention, an added novelty of reaction is the use of three equivalents of $BF_3.OEt_2$ in the formation of pyrylium salts which results in the column free isolation of the products by suppressing the side reactions. In this novel process of the pyrylium salts, two methods utilised. In the first method, α,β-unsaturated ketones are isolated prior to cyclisation and in the second method, without further purification or separation of α,β-unsaturated ketones, react with substituted alkynes insitu, which will be subjected to facilitate the cyclisation in the same reaction vessel.

In still another embodiment of the invention, all the reaction steps of said process were monitored by chromatography and the crude products obtained were subjected to purification using crystallization to get the pure compounds in good yields. Further, all the resultant compounds/products were systematically characterized using various analytical and spectral methods.

WORKING EXAMPLES

Following examples are given by way of illustration and therefore should not be construed to limit the scope of the invention.

Example 1

General Preparation of 2,4,6-triphenylpyrylium tetrafluoroborate [B1]

3 eq. of $BF_3.OEt_2$ (102.18 mg, 0.09 ml, 0.72 mmol), dissolved in 1 ml of cyclohexane is added to the mixture of phenyl acetylene (74 mg, 0.72 mmol), and Compound A1(E-Chalcone), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.24 mmol) in dry cyclohexane (2 ml) under the oxygen atmosphere. The solution was stirred for 3 hrs at 60° C. After completion of the reaction, the reaction mixture was poured in to 10 ml of diethyl ether dissolving the residue in DCM (5 ml), to precipitate the product. The product was filtered and washed with diethyl ether and dried in air. Recrystallization from ethanol afforded the compound 2,4,6-triphenylpyrylium tetrafluoroborate as yellow crystals; 62 mg (65%), m.p=225-227° C.; IR (neat, cm$^{-1}$): 3069, 2923, 1621 (—C=O+), 1592, 1468, 1272, 1194, 1049, 986, 763; $^1$H NMR (500 MHz, DMSO-d6): δ 7:84 8.67 (m, 15 aromatic H), 9.24 (s, 2H); $^{13}$C NMR (125 MHz, DMSO-d6): δ 115.1, 128.8, 129.1, 129.8, 129.9, 130.0, 132.4, 135.0, 135.2, 165.1, 170.0; HRMS $C_{23}H_{17}O^+$ ([M]$^+$): 309.1284.

Example 2

Preparation of 2,6-diphenyl-4-(p-tolyl)pyryliumtetrafluoroborate [B2]

3 eq. of $BF_3.OEt_2$ (102.18 mg, 0.08 ml, 0.72 mmol), dissolved in 1 ml of cyclohexane is added to the mixture of phenyl acetylene (68.63 mg, 0.67 mmol), and Compound A2 ((E)-1-phenyl-3-(p-tolyl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.22 mmol) in dry cyclohexane (2 ml) under oxygen atmosphere. The solution was stirred for 3 hrs at 60° C. After completion of the reaction, the reaction mixture was poured in to 10 ml of diethyl ether dissolving the residue in DCM (95 ml), to precipitate the product. The product was filtered and washed with diethyl ether and dried in air. Recrystallization from ethanol afforded the compound 2,6-diphenyl-4-(p-tolyl)pyrylium tetrafluoroborate as yellow crystals; 65 mg (70%), m.p=257-259° C.; IR (neat, cm$^{-1}$): 2920, 2851, 1624 (—C=O+), 1599, 1491, 1254, 1195, 1060, 1027, 822; $^1$H NMR (500 MHz, DMSO-d$_6$): δ 2.53 (s, 3H, —CH$_3$), 6.63-8.59 (m, 14 aromatic H), 79.41 (s, 2H); $^{13}$C NMR (125 MHz, DMSO-d$_6$): δ 21.4, 114.3, 128.7, 129.1, 129.5, 129.8, 130.2, 130.6, 134.9, 147.0, 164.6, 169.7; HRMS for $C_{24}H_{19}O^+$ ([M]$^+$): 323.1437.

Example 3

Preparation of 4-(4-methoxyphenyl)-2,6-diphenylpyrylium tetrafluoroborate [B3]

3 eq. of $BF_3.OEt_2$ (89.42 mg, 0.07 ml, 0.63 mmol), dissolved in 1 ml of cyclohexane is added to the mixture of phenyl acetylene (64.34 mg, 0.63 mmol), and Compound A3 ((E)-3-(4-methoxyphenyl)-1-phenylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether dissolving the residue in DCM (5 ml), to precipitate the product. The product was filtered and washed with diethyl ether and dried in air. Recrystallization from ethanol afforded the compound 4-(4-methoxyphenyl)-2,6-diphenylpyrylium tetrafluoroborate as red-orange crystals; 50 mg (56%), m.p=218-220° C.; IR (net, cm$^{-1}$): 3063, 2924, 2850, 1629 (—C=O+), 1576, 1442, 1246, 1186, 1055, 836; $^1$H NMR (500 MHz, DMSO-d$_6$): δ 4.01 (s, 3H, —OCH$_3$), 7.34-8.72 (m, 14 aromatic H), 9.06 (s, 2H); $^{13}$C NMR (125 MHz, DMSO-d$_6$): δ 61.5, 120.9, 129.6, 133.7, 134.5, 135.0, 139.9, 168.8, 171.1, 174.1; HRMS for $C_{24}H_{19}O_2^+$ ([M]$^+$): 339.1390.

Example 4

Preparation of 4-(4-hydroxyphenyl)-2,6-diphenylpyrylium tetrafluoroborate [B4]

3 eq. of $BF_3.OEt_2$ (93.67 mg, 0.08 ml, 0.66 mmol), dissolved in 1 ml of cyclohexane is added to the mixture of phenyl acetylene (67.04 mg, 0.66 mmol), and Compound A4 ((E)-3-(4-hydroxyphenyl)-1-phenylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.22 mmol) in dry cyclohexane (2 ml) under the oxygen atmosphere. The solution was stirred for 6 hrs, at 60° C. After completion of the reaction, the reaction mixture was poured in to 10 ml of diethyl ether dissolving the residue in DCM (5 ml), to precipitate the product. The product was filtered and washed with diethyl ether and dried in air. Recrystallization from ethanol afforded the compound 4-(4-hydroxyphenyl)-2,6-diphenylpyrylium tetrafluoroborate as orange crystals; 62 mg (67%), m.p=282-285° C.; IR (neat, cm$^{-1}$): 3343, 2972, 1633 (—C=O+), 1596, 1491, 1277, 1188, 1120, 1069, 844; $^1$H NMR (500 MHz, DMSO-d$_6$): δ 7.13-8.65 (m, 14 aromatic H), 8.99 (s, 2H), 11.41 (brs, 1H, —OH); $^{13}$C NMR (125 MHz, DMSO-d$_6$): δ 112.5, 117.1, 122.8, 128.3, 129.3, 129.7, 133.6, 134.5, 163.4, 165.7, 168.3; HRMS for $C_{23}H_{17}O_2^+$ ([M]$^+$): 325.1239.

Example 5

Preparation of 4-(4-bromophenyl)-2,6-diphenylpyrylium tetrafluoroborate [B5]

3 eq. of $BF_3.OEt_2$ (72.38 mg, 0.06 ml, 0.51 mmol), dissolved in 1 ml of cyclohexane is added to the mixture of phenyl acetylene (53.31 mg, 0.51 mmol), and Compound A5

((E)-3-(4-bromophenyl)-1-phenylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.17 mmol) in dry cyclohexane (2 ml) under the oxygen atmosphere. The solution was stirred for 3 hrs at 60° C. After completion of the reaction, the reaction mixture was poured in to 10 mi of diethyl ether dissolving the residue in DCM (5 ml), to precipitate the product. The product was filtered and washed with diethyl ether and dried in air. Recrystallization from ethanol afforded the compound 4-(4-bromophenyl)-2,6-diphenylpyrylium tetrafluoroborate as yellow crystals; 39 mg (48%), m.p=260-262° C.; IR (neat, cm$^{-1}$): 3057, 2920, 1617 (—C=O+), 1578, 1490, 1275, 1193, 1065, 777, 683; $^1$H NMR (500 MHz, DMSO-d$_6$): δ 7.82-8.61 (m, 14 aromatic H), 9.19 (s, 2H); $^{13}$C NMR (125 MHz, DMSO-d$_6$): δ 115.1, 128.8, 129.1, 129.9, 131.6, 131.8, 132.9, 135.1, 163.9, 170.2; HRMS for $C_{23}H_{16}BrO^+$ ([M]$^+$): 387.0384.

Example 6

Preparation of 4-(4-chlorophenyl)-2,6-diphenylpyrylium tetrafluoroborate [B6]

3 eq. of BF$_3$.OEt$_2$ (87.71 mg, 0.08 ml, 0.62 mmol), dissolved in 1 ml of cyclohexane is added to the mixture of phenyl acetylene (63.12 mg, 0.62 mmol), and Compound A6 ((E)-3-(4-chlorophenyl)-1-phenylprop-27en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether dissolving the residue in DCM (5 ml), to precipitate the product. The product was filtered and washed with diethyl ether and dried in air. Recrystallization from ethanol afforded the compound 4-(4-chlorophenyl)-2,6-diphenylpyrylium tetrafluoroborate as yellow crystals; 45 mg (51%), m.p=253-255° C.; IR (neat, cm$^{-1}$): 2921, 1622 (—C=O+), 1587, 1492, 1248, 1093, 1047, 825, 778, 731; $^1$H NMR (500 MHz, DMSO-d$_6$): δ 7.82-8.66 (m, 14 aromatic H), 9.19 (s, 2H); $^{13}$C NMR (125 MHz, DMSO-d$_6$): δ 115.2, 128.8, 129.1, 129.8, 129.9, 131.8, 135.2, 163.7, 170.2; HRMS for $C_{23}H_{16}ClO^+$ ([M]$^+$): 343.0883.

Example 7

Preparation of 4-(4-fluorophenyl)-2,6-diphenylpyrylium tetrafluoroborate [67]

3 eq. of BF$_3$.OEt$_2$ (94.09 mg, 0.08 ml, 0.66 mmol), dissolved in 1 ml of cyclohexane is added to the mixture of phenyl acetylene (67.71 mg, 0.66 mmol), and Compound A7 ((E)-3-(4-fluorophenyl)-1-phenylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.22 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in Recrystallization from ethanol afforded the compound 4-(4-fluorophenyl)-2,6-diphenylpyrylium tetrafluoroborate as yellow crystals; 59 mg (64%), m.p=208-210° C.; IR (neat, cm$^{-1}$): 3062, 2972, 1624 (—C=O+), 1493, 1269, 1166, 1120, 1036, 830, 777; $^1$H NMR (500 MHz, DMSO-d$_6$): δ 7.68-8.75 (m, 14 aromatic H), 9.16 (s, 2H); $^{13}$C NMR (125 MHz, DMSO-d$_6$): δ 114.9, 117.1, 117.2, 128.8, 129.1, 129.9, 133.2, 133.3, 135.1, 163.8, 169.9; HRMS for $C_{23}H_{16}FO^+$ ([M]$^+$): 327.1189.

Example 8

Preparation of 2,6-diphenyl-4-(4-(trifluoromethyl)phenyl)pyryliumtetrafluoroborate [B8]

3 eq. of BF$_3$.OEt$_2$ (77.07 mg, 0.07 ml, 0.54 mmol), dissolved in 1 ml of cyclohexane is added to the mixture of phenyl acetylene (55.47 mg, 0.54 mmol), and Compound A8 ((E)-1-phenyl-3-(4-(trifluoromethyl)phenyl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.18 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air.

Recrystallization from ethanol afforded the compound 2,6-diphenyl-4-(4-(trifluoromethyl)phenyl)pyryliumtetrafluoroborate as yellow crystals; 39 mg (47%), m.p=245-247° C.; IR (neat, cm$^{-1}$): 3109, 3077, 1622 (—C=O+), 1495, 1322, 1270, 1171, 1065, 1034, 836; $^1$H NMR (500 MHz, DMSO-d$_6$): δ 7.59-8.52 (m, 14 aromatic H), 9.03 (s, 2H); $^{13}$C NMR (125 MHz, DMSO-d$_6$): δ 116.3, 126.5, 128.9, 129.9, 130.7, 135.3, 136.5, 163.7, 170.7; HRMS Calcd. for $C_{24}H_{16}F_3O^+$ ([M]$^+$): 377.1159.

Example 9

Preparation of 4-(naphthalen-2-yl)-2,6-diphenylpyrylium tetrafluroborate [B9]

3 eq. of BF$_3$.OEt$_2$ (82.17 mg, 0.07 ml, 0.58 mmol), dissolved in 1 ml of cyclohexane is added to the mixture of phenyl acetylene (59.15 mg, 0.57 mmol), and Compound A9 ((E)-3-(naphthalen-211)-1-phenylprop-2-en-1-one), prepared by the method described by (T. M. Kadayato C. Park, K. Y. Jun, T. T. Magar, G. Bist, H. Y. Yoo, Y. Kwon and E. S. Lee, Bioorg. Med. Chem., 2015, 23, 3499) (50 mg, 0.19 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 4-(naphthalen-2-yl)-2,6-diphenylpyrylium tetrafluroborate as pale red crystals; 50 mg (58%), m.p=190-193° C.; IR (neat, cm$^{-1}$): 3061, 3029, 1611 (—C=O+), 1579, 1492, 1273, 1223, 1158, 777; $^1$H NMR (500 MHz, DMSO-d$_6$): δ 7.76-9.35 (m, 19 aromatic H); $^{13}$C NMR (125 MHz, DMSO-d$_6$): δ 115.0, 124.8, 127.8, 127.9, 128.8, 129.2, 129.5, 129.8, 129.9, 130.3, 132.5, 132.6, 135.0, 135.8, 164.7, 169.8; HRMS for $C_{27}H_{19}O^+$ ([M]$^+$): 359.1443.

Example 10

Preparation of 4-(furan-2-yl)-2,6-diphenylpyrylium tetrafluoroborate [610] 3 eq. of BF$_3$.OEt$_2$ (107.72 mg, 0.09 ml, 0.75 mmol), dissolved in 1 ml of cyclohexane is added to the mixture of phenyl acetylene (67.04 mg, 0.75 mmol), and Compound A10 ((E)-3-(furan-2-yl)-1-phenylprop-2-en-1-one), prepared by the method described by (T. M. Kadayat, C. Park, K. Y. Jun, T. T. Magar, G. Bist; H. Y. Yoo, Y. Kwon and E. S. Lee, Bioorg. Med. Chem., 2015, 23, 3499) (50 mg, 0.25 mmol) in dry cyclohexane (2 ml) under oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 4-(furan-2-yl)-2,6-diphenylpyrylium tetrafluoroborate as greenish black crystals; 69 mg (71%), m.p=202-204° C.; IR (neat, cm$^{-1}$): 3120, 3061, 1626 (—C=O+), 1581, 1495, 1377, 1266, 1063, 946, 766; $^1$H NMR (500 MHz, CD$_3$CN): δ 7.06 8.38 (m, 13 aromatic H), 8.49 (s, 2H); $^{13}$C NMR (125 MHz, CD$_3$CN): δ 111.6, 117.5, 126.6, 129.3, 130.1, 130.9, 136.1, 149.6, 154.7, 170.9; HRMS for C$_{21}$H$_{15}$O$_2^+$ ([M]): 299.1077.

Example 11

Preparation of 2,6-diphenyl-4-(thiophen-3-yl)pyryliumtetrafluroborate [B11]

3 eq. of BF$_3$.OEt$_2$ (99.21 mg, 0.09 ml, 0.0.69 mmol), dissolved in 1 ml of cyclohexane is added to the mixture of phenyl acetylene (71.38 mg, 0.69 mmol), and Compound A11 ((E)-1-phenyl-3-(thiophen-3-yl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.23 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2,6-diphenyl-4-(thiophen-3-yl)pyryliumtetrafluroborate as black crystals; 63 mg (67%), m.p=205-207° C.; IR (neat, cm$^{-1}$): 3104, 3062, 1622 (—C=O+), 1579, 1492, 1270, 1221, 1055, 775, 700; $^1$H NMR (500 MHz, DMSO-d$_6$): δ 7.82-9.51 (m, 15 aromatic H); $^{13}$C NMR (125 MHz, DMSO-d$_6$): δ 113.9, 127.6, 128.5, 129.2, 129.9, 134.9, 136.1, 138.2, 158.2, 169.7; HRMS for C$_{21}$H$_{15}$OS$^+$ ([M]$^+$): 315.0849.

Example 12

Preparation of 2-phenyl-4,6-di-p-tolylpyrylium tetrafluoroborate [B12]

3 eq. of BF$_3$.OEt$_2$ (90.01 mg, 0.08 ml, 0.72 mmol), dissolved in 1 ml of cyclohexane is added to the mixture of phenyl acetylene (64.36 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry Cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2-phenyl-4,6-di-p-tolylpyrylium tetrafluoroborate as orange crystals; 42 mg (48%), m.p=214-216° C.; IR (neat, cm$^{-1}$): 3124, 2923, 2855, 1624 (—C=O+), 1599, 1491, 1228, 1192 1055, 818; $^1$H NMR (500 MHz, DMSO-d$_6$): δ 2.49 (s, 6H, —CH$_3$), 7.56-8.99 (m, 15 aromatic H); $^{13}$C NMR (125 MHz, DMSO-d$_6$): 21.3, 21.4, 113.7, 113.8, 126.3, 128.5, 128.7, 129.1, 129.5, 129.8, 130.0, 130.5, 130.5, 134.7, 146.3, 146.9, 164.2, 169.1, 169.8; HRMS for C$_{25}$H$_{21}$O$^+$ ([M]$^+$): 337.1597.

Example 13

Preparation of 2,4-bis(4-methoxyphenyl)-6-phenylpyrylium tetrafluoroborate [B13]

3 eq. of BF$_3$.OEt$_2$ (80.90 mg, 0.07 ml, 0.57 mmol), dissolved in 1 ml of cyclohexane is added to the mixture of phenyl acetylene (58.23 mg, 0.57 mmol), and Compound A13 ((E)-1,3-bis(4-methoxyphenyl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.19 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2,4-bis(4-methoxyphenyl)-6-phenylpyrylium tetrafluoroborate as pale-red crystals; 43 mg (51%), m.p=245-247° C.; IR (neat, cm$^{-1}$): 3161, 3073, 2923, 1629 (—C=O+), 1589, 1467, 1246, 1056, 951, 836; $^1$H NMR (500 MHz, DMSO-d$_6$): δ 3.98-3.99 (m, 6H, —CH$_3$), 7.31-8.93 (m, 15 aromatic H); $^{13}$C NMR (125 MHz, DMSO-d$_6$): δ 56.0, 56.1, 111.9, 115.4, 121.3, 124.3, 128.1, 129.3, 129.7, 131.0, 132.7, 134.3, 162.5, 164.8, 165.5, 167.5, 168.9; HRMS for C$_{25}$H$_{21}$O$_3^+$ ([M]$^+$): 369.1496.

Example 14

Preparation of 2,4-bis(4-chlorophenyl)-6-phenylpyrylium tetrafluoroborate [B14]

3 eq. of BF$_3$.OEt$_2$ (77.06 mg, 0.07 ml, 0.54 mmol), dissolved in 1 ml of cyclohexane is added to the mixture of phenyl acetylene (55.16 mg, 0.54 mmol), and Compound A14 ((E)-1,3-bis(4-chlorophenyl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.18 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2,4-bis(4-chlorophenyl)-6-phenylpyrylium tetrafluoroborate as yellow crystals; 42 mg (50%), m.p=243-245° C.; IR (neat, cm$^{-1}$): 3070, 2922, 1621 (—C=O+), 1586, 1490, 1226, 1121, 1051, 829, 723; $^1$H NMR (500 MHz, DMSO-d$_6$): δ 7.81 8.64 (m, 13 aromatic H), 9.18 (s, 2H); $^{13}$C NMR (125 MHz, DMSO-d$_6$): δ 115.3, 127.9, 128.8, 128.9, 129.8, 130.0, 130.5, 131.1, 131.8, 135.3, 140.3, 140.6, 163.7, 169.0, 170.3; HRMS for $C_{23}H_{15}Cl_2O^+$ ([M]$^+$): 377.0509.

Example 15

Preparation of 2,4-bis(4-bromophenyl)-6-phenylpyrylium tetrafluoroborate [B15]

3 eq. of BF$_3$.OEt$_2$ (58.33, 0.05 ml, 0.14 mmol), dissolved in 1 ml of cyclohexane is added to the mixture of phenyl acetylene (42.11 mg, 0.14 mmol), and Compound A15 ((E)-1,3-bis(4-bromophenyl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.14 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2,4-bis(4-bromophenyl)-6-phenylpyrylium tetrafluoroborate as yellow crystals; 27 mg (36%), m.p=255-257° C.; IR (neat, cm$^{-1}$): 3063, 2922, 1622 (—C=O+), 1581, 1493, 1266, 1244, 1055, 821, 722; $^1$H NMR (500 MHz, DMSO-d$_6$): δ 7.82-8.61 (m, 13 aromatic H), 9.20 (s, 2H); $^{13}$C NMR (125 MHz, DMSO-d$_6$): 115.2, 115.3, 128.3, 128.9, 129.0, 129.5, 129.9, 130.1, 130.5, 131.5, 131.8, 132.9, 133.0, 135.3, 163.9, 169.2, 170.4; HRMS for $C_{23}H_{15}Br_2O^+$ ([M]$^+$): 464.9489.

Example 16

Preparation of 2,4-bis(4-fluorophenyl)-6-phenylpyrylium tetrafluoroborate [B16]

3 eq. of BF$_3$.OEt$_2$ (85.16 mg, 0.07 ml, 0.60 mmol), dissolved in 1 ml of cyclohexane is added to the mixture of phenyl acetylene (62.52 mg, 0.61 mmol), and Compound A16 ((E)-1,3-bis(4-fluorophenyl)prop-2-en-1-one), prepared by the method, described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.20 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound name as yellow crystals; 51 mg (57%), m.p=190-192° C.; IR (neat, cm$^{-1}$): 3068, 2923, 1626 (—C=O+), 1595, 1496, 1271, 1165, 1051, 834, 774; $^1$H NMR (500 MHz, DMSO-d$_6$): δ 7.66-9.15 (m, 15 aromatic H); $^{13}$C NMR (125 MHz, DMSO-d$_6$): δ 114.7, 114.8, 117.1, 117.1, 117.2, 117.3, 125.8, 128.8, 128.9, 129.0, 129.8, 131.9, 132.0, 133.2, 133.3, 135.1, 163.7, 165.1, 169.0, 169.9; HRMS for $C_{23}H_{15}F_2O^+$ ([M]$^+$): 345.1092.

Example 17

Preparation of 2-phenyl-4,6-di(thiophen-3-yl)pyryliumtetrafluoroborate [B17]

3 eq. of BF$_3$OEt$_2$ (97.93 mg, 0.08 ml, 0.69 mmol), dissolved in 1 ml of cyclohexane is added to the mixture of phenyl acetylene (69.65 mg, 0.68 mmol), and Compound A17 ((E)-1,3-di(thiophen-3-yl)prop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.23 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2-phenyl-4,6-di(thiophen-3-yl)pyryliumtetrafluoroborate as black crystals; 70 mg (76%), m.p=219-221° C.; IR (neat, cm$^{-1}$): 3106; 2964, 1622 (—C=O+), 1513, 1445, 1264, 1224, 1059, 889, 765; $^1$H NMR (500 MHz, DMSO-d$_6$): δ 7.67-9.30 (m, 13 aromatic H); $^{13}$C NMR (125 MHz, DMSO-d$_6$): δ 113.1, 113.8, 126.4, 127.5, 128.3, 129.0, 129.7, 129.9, 132.0, 134.6, 135.3, 136.1, 137.7, 157.9, 165.6, 168.5; HRMS for $C_{19}H_{13}OS_2^+$ ([M]$^+$): 321.0412.

Example 18

Preparation of 2,4,6-tri-p-tolylpyrylium tetrafluoroborate [B18]

3 eq. of BF$_3$.OEt$_2$ (89.42 mg, 0.08 ml, 0.0.63 mmol), dissolved in 1 ml of cyclohexane is added to the mixture of 4-Ethynyltoluene (73.18 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2,4,6-tri-p-tolylpyrylium tetrafluoroborate as yellow crystals; 54 mg (58%), m.p=251-253° C.; IR (neat, cm$^{-1}$): 3129, 3039, 2921, 1624 (—C=O+), 1599, 1494, 1256, 1191, 1055, 817, $^1$H NMR (500 MHz, DMSO-d$_6$): δ 7.54 8.48 (m, 12 aromatic H), 8.94 (s, 2H); $^{13}$C NMR (125 MHz, DMSO-d$_6$): δ 21.4, 21.4, 113.3, 126.4, 128.5, 129.9, 130.4, 146.1, 146.7, 163.9, 169.3; HRMS for $C_{26}H_{23}O+$([M]$^+$): 351.1749.

Example 19

Preparation of 2-(4-bromophenyl)-4,6-di-p-tolylpyrylium tetrafluoroborate [B19]

3 eq. of BF$_3$.OEt$_2$ (89.42 mg, 0.08 ml, 0.63 mmol), dissolved in 1 ml of cyclohexane is added to the mixture of 1-bromo-4-ethynylbenzene (114.05 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2-(4-bromophenyl)-4,6-di-p-tolylpyrylium tetrafluoroborate as orange crystals; 50 mg (47%), m.p=270-272° C.; IR (neat, cm$^{-1}$): 3109, 3030, 2854, 1624 (—C=O$_+$), 1598, 1498, 1230, 1192, 1055, 1004; $^1$H NMR (500 MHz, DMSO-d$_6$): δ 7.61-8.55 (m, 12 aromatic H), 9.09 (s, 2H); $^{13}$C NMR (125 MHz, DMSO-d$_6$): δ 21.4, 21.5, 113.9, 126.2, 128.3, 128.7, 129.1, 129.4, 130.1, 130.2, 130.5, 130.5, 132.8, 146.5, 147.1, 164.2, 168.0, 169.9; HRMS for C$_{25}$H$_{20}$BrO$^+$ ([M]$^+$): 415.0645.

Example 20

Preparation of 2-(4-n-propylphenyl)-4,6-di-p-tolylpyrylium tetrafluoroborate [1320]

3 eq. of BF$_3$.OEt$_2$ (89.42 mg, 0.08 ml, 0.63 mmol), dissolved in 1 ml of cyclohexane is added to the mixture of 1-ethynyl-4-propylbenzene (91.21 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2-(4-propylphenyl)-4,6-di-p-tolylpyrylium tetrafluoroborate as orange crystals; 53 mg (54%), m.p 252-254° C.; IR (neat, cm$^{-1}$): 3114, 3039, 2928 (—C=O+), 2869, 1625, 1600, 1496, 1273, 1055, 818; $^1$H NMR (500 MHz, DMSO-d$_6$): δ 0.95 (t, 3H, —CH$_3$), 1.69 (st, 2H, —CH$_2$), 2.75 (t, 2H, —CH$_2$), 7.58-8.52 (m, 12 aromatic H), 9.00 (s, 2H); $^{13}$C NMR (125 MHz; DMSO-d$_6$): δ 13.6, 21:4, 21.4, 23.6, 37.2, 113.2, 113.3, 126.3, 126.6, 128.5, 128.6, 129.4, 129.8, 129.9, 130.4, 146.1, 146.7, 150.4, 163.8, 169.3; HRMS for C$_{28}$H$_{25}$O$^+$ ([M]$^+$): 379.2056. Found: 379.2055.

Example 21

Preparation of 2-(4-fluorophenyl)-4,6-di-p-tolylpyrylium tetrafluoroborate [B21]

3 eq. of BF$_3$.OEt$_2$ (89.42 mg, 0.08 ml, 0.63 mmol), dissolved in 1 ml of cyclohexane is added to the mixture of 1-ethynyl-4-fluorobenzene (76.19 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. kwon and E. S. Lee, Bioorg. Med. Chem.; 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in, air. Recrystallization from ethanol afforded the compound 2-(4-fluorophenyl)-4,6-di-p-tolylpyrylium tetrafluoroborate as orange crystals; 41 mg (44%), m.p.=242-244° C.; IR (neat, cm-1): 2968, 2922, 1626 (—C=O+), 1599, 1492, 1348, 1194, 1165, 1055, 845; $^1$H NMR (500 MHz, DMSO-d$_6$): δ 7.61-9.05 (m, 14 aromatic H); $^{13}$C NMR (125 MHz, DMSO-d$_6$): 21.4, 21.4, 113.5, 113.6, 117.0, 117.2, 125.8, 126.3, 128.7, 129.4, 130.0, 130.4, 130.5, 131.6, 131.7, 146.3, 146.9, 164.2, 164.9, 168.1, 169.7; HRMS for C$_{25}$H$_{20}$FO$^+$ ([M]$^+$): 355.1501.

Example 22

Preparation of 2-(thiophen-3-yl)-4,6-di-p-tolylpyrylium tetrafluoroborate [B22]

3 eq. of BF$_3$.OEt$_2$ (89.42 mg, 0.08 ml, 0.63 mmol), dissolved in 1 ml of cyclohexane is added to the mixture of 3-ethynylthiophene (68.46 mg, 0.63 mmol), and Compound A12 ((E)-1,3-di-p-tolylprop-2-en-1-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound 2-(thiophen-3-yl)-4,6-di-p-tolylpyrylium tetrafluoroborate as black colour crystals; 89 mg (98%), m.p=232-234° C.; IR (neat, cm$^{-1}$): 3108, 2920, 2851, 1625 (—C=O+), 1599, 1495, 1266, 1193, 1057, 817; $^1$H NMR (500 MHz, DMSO-d$_6$): δ 7.60-9.26 (m, 14 aromatic H); $^{13}$C NMR (125 MHz, DMSO-d$_6$): δ 21.4, 21.4, 112.9, 113.6, 126.3, 128.6, 129.5, 129.8, 130.4, 130.5, 132.1, 146.0, 146.6, 0.164.1, 165.2, 168.8; HRMS for C$_{23}$H$_{16}$OS$^+$ ([M]$^+$): 343.1164.

Example 23

Preparation of 2,4,6-triphenylpyrylium trifluoromethanesulfonate [D1]

3 eq. of HOTf (108.06 mg, 0.06 ml, 0.72 mmol), is added to the mixture of phenyl acetylene (74 mg, 0.72 mmol), and Compound A1 (E-Chalcone), prepared by the method described by T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.24 mmol) in dry cyclohexane (2 ml) under the oxygen atmosphere. The solution was stirred for 3 hrs at 60° C. After completion of the reaction, the reaction mixture was poured in to 10 ml of diethyl ether dissolving the residue in DCM (5 ml), to precipitate the product. The product was filtered and washed with diethyl ether and dried in air. Recrystallization from ethanol afforded the compound 2,4,6-triphenylpyrylium trifluoromethanesulfonate as yellow crystals; 53 mg (48%), m.p=252-254° C.; IR (neat, cm$^{-1}$): 2920, 2851, 1622, (—C=O+), 1594, 1499, 1471, 1254, 1144, 1031, 770, 641; $^1$H NMR (500 MHz, DMSO-d6): δ 7.79-8.94 (m, 15 aromatic H), 9.19 (s, 2H); $^{13}$C NMR (125 MHz, DMSO-d6): 115.7, 129.3, 129.6, 130.3, 130.4, 130.5, 132.9, 135.5, 135.7, 165.6, 170.6; HRMS C$_{23}$H$_{17}$O$^+$ ([M]$^+$): 309.1278.

Example 24

Preparation of 2,4-diphenyl-5,6-dihydrobenzo[h]chromen-1-ium tetrafluoroborate [D2]

3 eq. of BF$_3$.OEt$_2$ (89.42 mg, 0.08 ml, 0.63 mmol), dissolved in 1 ml of cyclohexane is added to the mixture of phenyl acetylene (64.45 mg, 0.63 mmol), and Compound C1 ((E)-2-benzylidene-3,4-dihydronaphthalen-1(2H)-one), prepared by the method described by (T. M. Kadayat, C. Park, K. Y. Jun, T. T. Magar, G. Bist, H. Y. Yoo, Y. Kwon and E. S. Lee, Bioorg. Med. Chem., 2015, 23, 3499) (50 mg, 0.21 mmol) in dry cyclohexane (2 ml) under the oxygen atmosphere. The solution was stirred for 3 hrs at 60° C. After completion of the reaction, the reaction mixture was poured in to 10 ml of diethyl ether, dissolving the residue in DCM (5 ml), to precipitate the product. The product was filtered and washed with diethyl ether and dried in air. Recrystallization from ethanol afforded the compound name as yellow crystals; 43 mg (48%), m.p=248-250° C.; IR (neat, cm-1): 3066, 2851, 1612 (—C═O+), 1596, 1493, 1386, 1243, 1053, 881, 728; $^1$H NMR (500 MHz, DMSO-$d_6$): δ 3.09 (t, 2H, —CH$_2$), 3.25 (t, 2H, —CH$_2$), 7.59-8.55 (m, 14 aromatic H), 8.84 (s, 1H); $^{13}$C NMR (125 MHz, DMSO-$d_6$): δ 24.2, 25.7, 119.1, 125.9, 126.8, 128.4, 128.4, 128.8, 128.9, 129.2, 129.3, 129.4, 129.9, 132.1, 134.0, 1347, 135.6, 142.0, 165.8, 166.6, 167.4; HRMS for $C_{25}H_{19}O^+$ ([M]$^+$): 335.1435; HRMS for $C_{25}H_{19}O^+$ ([M]$^+$): 335.1435.

ADVANTAGES OF THE INVENTION

The various advantages of the present process are given below.
1. The present invention provides an industrially viable and cost effective process for the preparation of symmetrical and unsymmetrical pyrylium salts.
2: In the present invention, we have developed a four component, two-step process for the synthesis of variety of symmetrical and unsymmetrical pyrylium salts.
3. The process is conducted under the oxygen atmosphere; there are no side products observed which apparently improved the yields of the products.

The invention claimed is:
1. A process for the preparation of salt having the general formula I,

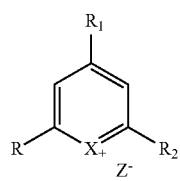

I wherein, in formula I:
X is oxygen;
R is selected from the group consisting of:
  a phenyl radical having substitution selected from CH$_3$, OCH$_3$, OH, Br, Cl, F, or CF$_3$;
  a heteroaryl radical selected from substituted thiophene-or substituted furan;
  a naphthyl radical; and
  a fused cyclohexyl and octahydro naphthalenyl radical;
R$_1$ is selected from the group consisting of:
  a phenyl radical having a substitution selected from CH$_3$, OCH$_3$, OH, Br, Cl, F, or CF$_3$; and
  a heteroaryl radical selected from substituted thiophene or substituted furan; and
R$_2$ is selected from the group consisting of:
  a phenyl radical having a substitution selected from CH$_3$, OCH$_3$, OH, Br, Cl, F, or CF$_3$;
  a heteroaryl radical selected from substituted thiophene or substituted furan; and a phenyl radical substituted with alkyl chain of three carbon atoms; and
Z is an anionic function selected from either BF$_4^-$ or HOTf$^-$; said process comprising the steps of:
a) condensing

with

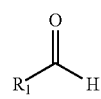

in the presence of NaOH to yield

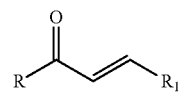

b) cyclizing the

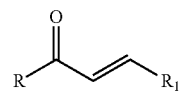

obtained in step (a) by either treating with

and BF$_3$.OEt$_2$, or treating with

and HOTf– in cyclohexane at 60° C.-70° C., and stirring for three to six hours under an oxygen atmosphere to obtain a reaction mixture;
c) pouring the reaction mixture obtained in step (b) into diethyl ether to precipitate a product;
d) washing the product with diethyl ether and drying the product in air; and
e) crystallizing from ethanol to obtain a salt having the general formula I.
2. The process as claimed in claim 1, wherein R or R$_1$ is a phenyl radical having a substitution selected from a group consisting of Cl, Br, and F.
3. The process as claimed in claim 1, wherein R or R$_1$ is a phenyl radical having a substitution selected from a group consisting of CH$_3$, OCH$_3$, OH, and CF$_3$.
4. The process as claimed in claim 1, wherein R is naphthyl radical.
5. The process as claimed in claim 1, wherein R or R$_1$ consists of substituted furan or substituted thiophene.

6. The process as claimed in claim 1, wherein
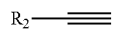
is phenyl acetylene and is substituted at para position with an alkyl chain of three carbon atoms.
* * * * *